United States Patent [19]

Derr, Jr. et al.

[11] Patent Number: 4,684,756
[45] Date of Patent: Aug. 4, 1987

[54] PROCESS FOR UPGRADING WAX FROM FISCHER-TROPSCH SYNTHESIS

[75] Inventors: W. Rodman Derr, Jr., Vincentown; William E. Garwood, Haddonfield; James C. Kuo, Cherry Hill; Tiberiu M. Leib, Voorhees; Donald M. Nace, Woodbury; Samuel A. Tabak, Wenonah, all of N.J.

[73] Assignee: Mobil Oil Corporation, New York, N.Y.

[21] Appl. No.: 858,620

[22] Filed: May 1, 1986

[51] Int. Cl.[4] .............................................. C07C 1/20
[52] U.S. Cl. ................................. 585/330; 518/700; 518/705; 585/314; 585/315; 585/408; 585/469; 585/640
[58] Field of Search ............... 585/469, 330, 408, 638, 585/344, 315, 316, 329; 518/700, 705

[56] References Cited
U.S. PATENT DOCUMENTS

| 4,125,566 | 11/1978 | Trin Dinh et al. | 585/469 |
| 4,133,841 | 1/1979 | Cosyns et al. | 585/469 |
| 4,252,736 | 2/1983 | Haag et al. | 585/638 |
| 4,423,265 | 12/1983 | Chu et al. | 585/322 |
| 4,471,145 | 9/1984 | Chu et al. | 585/322 |

Primary Examiner—A. Pal
Attorney, Agent, or Firm—Alexander J. McKillop; Michael G. Gilman; L. G. Wise

[57] ABSTRACT

The waxy liquid phase of an oil suspension of Fischer-Tropsch catalyst containing dissolved wax is separated out and the wax is converted by hydrocracking, dewaxing or by catalytic cracking with a low activity catalyst to provide a highly olefinic product which may be further converted to premium quality gasoline and/or distillate fuel.

5 Claims, 2 Drawing Figures

PROCESS FOR UPGRADING WAX FROM FISCHER-TROPSCH SYNTHESIS

The Government of the United States of America has rights in this invention pursuant to Contract No. DE-AC22-83PC60019 awarded by the U.S. Department of Energy.

NATURE OF THE INVENTION

This invention is concerned with a process wherein the "wax" resulting from the Fischer-Tropsch synthesis reaction is catalytically upgraded into high quality gasoline and distillate products.

PRIOR ART

Processes are well known for converting coal and other hydrocarbons, such as natural gas, to a gaseous mixture consisting primarily of hydrogen and carbon monoxide and/or dioxide. It is also well known that these gases (synthesis gas) will undergo conversion to reduction products of carbon monoxide such as hydrocarbons, over a fairly wide variety of catalysts under certain conditions of temperature and pressure. The Fischer-Tropsch process, for example, produces a range of liquid hydrocarbons, a portion of which have been used as low octane gasoline..More recently, it has been discovered that the conversion of synthesis gas into valuable products can be greatly enhanced by employing a special type of crystalline zeolite, exemplified by ZSM-5 in admixture with a carbon monoxide reduction catalyst. It has also been discovered that a highly aromatic or highly olefinic gasoline of enhanced octane number or a gasoline plus distillate mixture, can be obtained in greater yield from synthesis gas utilizing a selected synthesis gas composition of low $H_2/CO$ ratio in a relatively special Fischer-Tropsch syngas conversion operation and in a sequentially arranged dual reactor conversion process. Such a process is described in U.S. Pat. No. 4,279,830 which is incorporated herein by reference.

In conjunction with a Fischer-Tropsch process, there has been developed more recently the slurried catalyst reactor system. The slurried catalyst reactor system, otherwise identified herein as a Fischer-Tropsch catalyst suspended in a liquid medium suitable for the purpose of converting syngas to hydrocarbon products, has been the subject of numerous patents. Early patents on the subject are U.S. Pat. Nos. 2,438,029; 2,680,126; 2,775,607; 2,852,350 and numerous others.

This system can otherwise be described as a solid Fischer-Tropsch catalyst suspended in a liquid medium suitable for the purpose of converting syngas to heavier hydrocarbon products. The slurried catalyst reactor system is discussed in U.S. Pat. No. 4,252,736 which is incorporated herein by reference. The particular reactor system is also discussed extensively in the article, "Fischer-Tropsch Synthesis in Slurry Phase", M. D. Schlesinger et al, Industrial Engineering Chemistry, Volume 43, No. 6, page 1474 (1951). Basically, the slurried catalyst process constitutes a process in which a finely divided Fischer-Tropsch catalysts, such as Fe, suspended in oil is circulated by natural convection through a reactor in the presence of a synthesis gas. U.S. Pat. No. 4,252,736 discloses a process in which synthesis gas is first bubbled through a column of Fischer-Tropsch catalyst suspended in oil. The vaporous effluent is then flowed through a bed of zeolite (ZSM-5) and hydrocarbons boiling in the range of gasoline and distillate fuels are recovered from this second effluent.

In any process using a slurried catalyst to convert the syngas to higher molecular weight hydrocarbons, it has been noted that when low yields of light gases are produced, a large fraction of the hydrocarbon products is a heavy $C_{15+}$ wax. This product wax has to be separated from the catalyst and further upgraded to valuable products. U.S. Pat. No. 4,423,265 discloses a process wherein the liquid carrier in a Fischer-Tropsch synthesis slurry reactor system is periodically or continually separated. The catalyst is removed from the liquid carrier and the liquid carrier is subjected to isomerization and cracking and a portion of the cracked and isomerized product is then returned with the catalyst to the reactor zone while the remainder of the product is recovered as a desired hydrocarbon or gasoline fraction. U.S. Pat. No. 4,423,265 is incorporated herein by reference.

SUMMARY OF THE INVENTION

Figure 1:
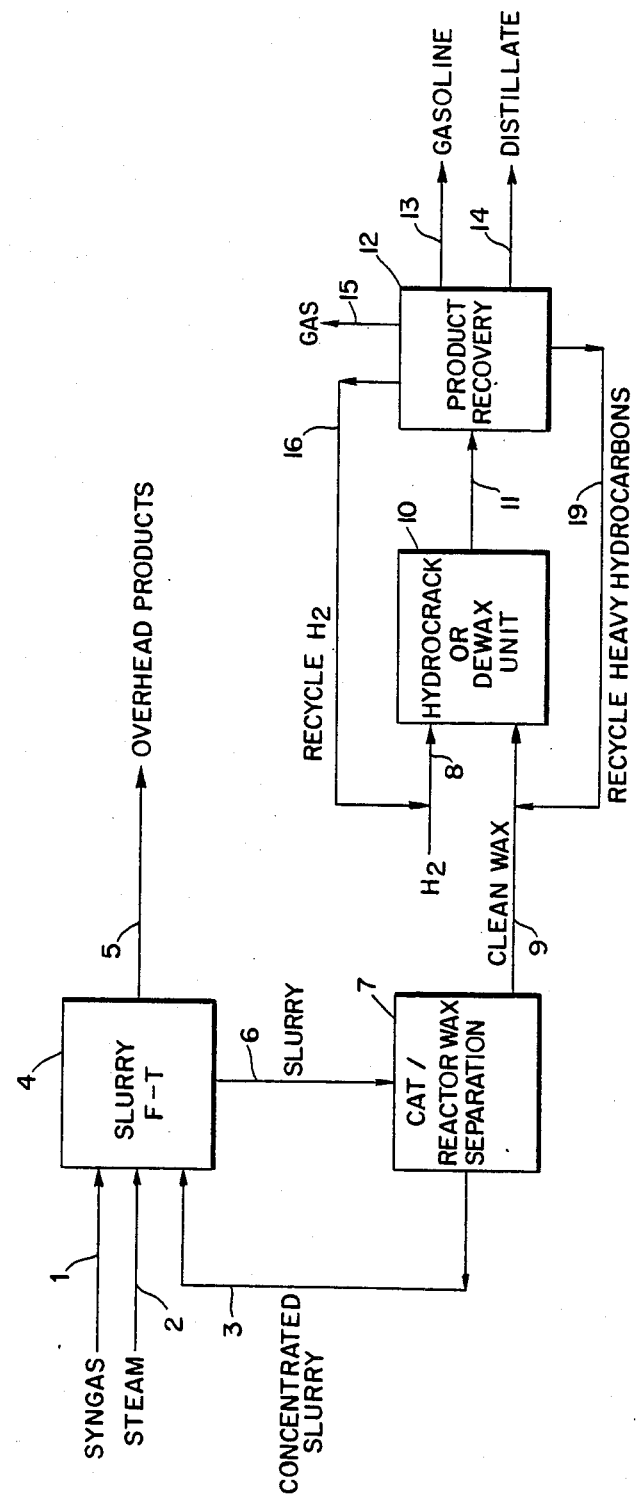
FIG. 1 is a flow diagram of one embodiment of the invention wherein Fischer-Tropsch synthesis wax is upgraded by hydrocracking or dewaxing.

In order to minimize light gas and maximize liquid fuel production, the Fischer-Tropsch synthesis is carried out with a low $H_2/CO$ ratio syngas in a slurried liquid phase catalyst reactor system to produce substantial yields of reactor-wax and low yields of methane plus ethane. The reactor wax, which is a high molecular weight highly paraffinic product, is thereafter upgraded by specialized cracking, hydrocracking or dewaxing processes to obtain premium quality gasoline and/or distillate fuel with minimal light gas production, thereby improving the overall product value.

DESCRIPTION OF THE INVENTION

An important aspect of this invention is directed to converting relatively low $H_2/CO$ ratio syngas (1/1 or less $H_2/CO$ ratio) wherein it is essential that the CO reducing catalyst used include water-gas shift activity or be characterized so that steam formed in the Fischer-Tropsch operation will react with charged CO to form $H_2$. Examples of CO reducing catalysts having shift activity are iron alone, or iron, cobalt or ruthenium provided with an added shift catalyst component. Shift catalysts suitable for the process include those containing the elements Fe, Cr, Zn, Cu or K. It is also contemplated charging some steam with syngas of 0.7 $H_2/CO$ ratio or less.

The low $H_2/CO$ ratio syngas, 0.5 to 1, and more usually in the range of 0.5 to about 0.8, is obtained by gasification of coals or lignites in advanced type gasifiers such as the BGC/Lurgi slagger. The syngas is converted in the slurried catalyst Fischer-Tropsch reactor (SFT) operation at a temperature within the preferred range of 400° F. up to about 600° F. and a pressure within the range of 50 to 700 psig. The contact time of the syngas is chosen to provide high conversion per pass, at least 50%, preferably 70 to 95%. This value depends on the length of reactor, the feed composition, the nature of the Fischer-Tropsch catalyst and its concentration in the slurry. The preferred catalyst is a composition of iron, potassium and copper that has been calcined and pretreated with CO and $H_2$ gas. A space velocity between about 1 liter and 10 liters of syngas (STP) per gram iron per hour will provide the desired high conversion. Within these operating parameters the temperature change is very small within narrow limits, thereby contributing to a more satisfactory operation of the system for producing desired liquid wax products in high yields. The suspended catalyst particles retained in the liquid phase may have particle sizes within the range of about 1 to 50 microns, thereby providing a larger amount of catalyst surface area than obtainable with larger sized catalyst particles or extrudate used in fluid and fixed catalyst bed systems. The low temperature operation contemplated is particularly desirable for reducing the production of $C_1$ and $C_2$ hydrocarbons, for reducing carbon build-up on the catalyst and for improving selectivity of the operation for producing high yields of reactor-wax which are highly paraffinic and of high molecular weight.

In FIG. 1, synthesis gas feed is introduced to reactor 4 through line 1. Reactor 4 contains a slurry of a Fischer-Tropsch catalyst in reactor-wax. The synthesis gas is obtained by gasification of western coal with a slagging gasifier such as the BGC/Lurgi and is preferably treated to remove sulfur and carbon dioxide prior to feeding to the slurried Fischer-Tropsch catalyst reactor (SFT). In this illustration, the composition of the synthesis gas is exemplified in Table 1.

TABLE 1

| Composition | Mol. % |
|---|---|
| $H_2$ | 29.83 |
| $C_1$ | 7.02 |
| CO | 60.26 |
| $CO_2$ | 2.21 |
| $N_2$ | 0.34 |
| $C_2=$ | 0.02 |
| $C_2$ | 0.32 |
| Total | 100.00 |

To raise the $H_2/CO$ ratio of the synthesis gas, the stoichiometric amount of steam is added through line 2 to promote shift activity and raise the ratio to 0.67. The shift reaction takes place in the SFT reactor without affecting activity of the Fischer-Tropsch catalyst. In reactor 4, the synthesis gas will undergo catalytic conversion to form reduction products of carbon monoxide, such as oxygenates and hydrocarbons, at temperatures in the range of about 300° F. to 850° F., under pressures of one to two hundred atmospheres over a wide selection of catalyst compositions. In this process scheme, synthesis gas is introduced to reactor 4 under a pressure of 402 psig at a temperature of 440° F., a space velocity (NL/g Fe-hr) of 3.5, and is converted over a co-precipitated iron-potassium-copper catalyst (0–3 wt.% each of $K_2CO_3$ and Cu based on iron) to produce a mixture consisting of hydrocarbons from methane to $C_{100+}$ and oxygenated compounds, mostly alcohols. A simplified overall yield distribution is set forth in Table 2 below.

In another example, a portion of the synthesis gas can be treated with a proper quantity of steam in a separate water-gas shift unit to convert CO into $H_2$ so that the overall $H_2/CO$ ratio becomes 0.6–0.7.

TABLE 2

| SFT YIELD Wt. % of (CO + $H_2$) Feed | | |
|---|---|---|
| $H_2O$ | 0.81 | |
| $H_2$ | 1.14 | |
| CO | 9.54 | |
| $CO_2$ | 65.95 | |
| $C_1$ | 0.75 | |
| $C_2=$ | 0.42 | |
| $C_2$ | 0.15 | |
| $C_3=$ | 0.66 | |
| $C_3$ | 0.18 | |
| $C_4=$ | 0.58 | |
| $C_4$ | 0.22 | |
| $C_5=$ | 0.96 | |
| $C_5$ | 0.29 | |
| $C_6$-$C_9$ (P + O) | 2.57 | Sp. Gr. = 0.70; MW = 101.77 |
| $C_{10}$-$C_{15}$ (P + O) | 2.17 | |
| $C_{16}$-$C_{20}$ (P + O) | 0.75 | |
| $C_{21}+$ (P + O) excl. wax | 0.18 | |
| Org. Acids | 0.03 | |
| Alcohol & Ketones | 0.78 | |
| $C_4$-$C_9$ Oxygenated HC's | 0.39 | |
| $C_{10}$-$C_{15}$ Oxygenated HC's | 0.17 | |
| $C_{16}$-$C_{20}$ Oxygenated HC's | 0.03 | |
| Slurry Wax | 11.23 | Sp. Gr. = 0.87; MW = 821.41 |
| | 100.00 | |

| Total Hydrocarbons as Wt. % (CO + $H_2$) = 22.56 | |
|---|---|
| $C_1$-$C_2$ | 6. Wt. % of HC |
| $C_3$-$C_4$ | 7.0 Wt. % of HC |
| $C_5$ | 34. Wt. % of HC |
| Wax | 50. Wt. % of HC |
| Oxygenates | 3. Wt. % of HC |

The SFT Fischer-Tropsch synthesis reaction products include about 5 to 25 wt.% olefins, 5 to 25 wt.% oxygenates and 30 to 85 wt.% of $C_{15+}$ reactor wax is highly paraffinic and has an average molecular weight of 400 to 1300. In a high reactor-wax yield operation, the wax produced may contain as high as 65 to 75 wt.% of $C_{55+}$ hydrocarbons. The SFT reactor-wax is further characterized as containing little or no aromatics, naphthenes, sulfur or nitrogen.

In a similar manner SFT reactor-waxes were produced from the synthesis gas of Table 1 under the following conditions to yield synthesis waxes having the composition and analysis shown below in Table 3. The conversion was carried out over an iron catalyst containing copper and potassium within the amounts of 0.1 to 1.5 wt.%, based on the iron. It should be understood, however, that any wax resulting from the Fischer-Tropsch synthesis reaction may be used in accordance with the invention and that high quality gasoline and distillate products also can be produced from Fischer-Tropsch waxes obtained by non-slurry phase operations.

TABLE 3

| | Run No | | | | |
|---|---|---|---|---|---|
| Conditions | 3 | 4 | 5 | 7 | 13 |
| $H_2$ + CO partial pressure, psig | 215 | 365 | 215 | 329 | 215 |
| Average Temp., °F. | 500 | 495 | 464–482 | 496 | 496 |
| S.V.[1] | 2.75 | 3 | 3–6 | 3.5 | 2.4 |
| $H_2/CO$ molar ratio | .6–.7 | .6–.7 | .6–.7 | .6–.7 | .6–.7 |
| Hydrocarbon Selectivity, Wt. % | | | | | |
| Methane + ethane yield | 9 | 4 | 2–4 | 5 | 2–4 |
| Reactor wax yield | 8 | 50 | 57–85 | 50 | 50–65 |

[1]Expressed as normal liter of $H_2$ + CO per gram iron/hour.

TABLE 3-continued

Composition of SFT Reactor-Waxes

| Carbon Number | Run No | | |
|---|---|---|---|
| | 3 | 4 | 5 |
| 10–20 | 7.7 | 1.9 | 1.5 |
| 21–25 | 15.1 | 3.9 | 3.1 |
| 26–30 | 19.8 | 6.2 | 3.9 |
| 31–35 | 17.9 | 6.6 | 4.3 |
| 36–40 | 13.2 | 5.3 | 3.5 |
| 41–45 | 9.7 | 4.6 | 3.3 |
| 46–50 | 6.7 | 4.1 | 3.1 |
| 51–55 | 3.9 | 2.6 | 2.6 |
| 55+ | 6.0 | 64.8 | 74.7 |
| Total | 100.0 | 100.0 | 100.0 |

Analysis of SFT Reactor-Waxes

| | Run No | | |
|---|---|---|---|
| | 3 | 4 | 5 |
| $C_{55}+$ Content, wt. % Based on FIMS[1] | 6 | 64 | 72 |
| $C_{55}+$ Content Based on GC, wt. % | 6 | 65 | 75 |
| Molar Avg. MW | 460 | 814 | 976 |
| (Avg. Carbon No.) | (33) | (58) | (70) |
| Weight Avg. MW | 596 | 1,135 | 1,291 |
| (Avg. Carbon No.) | (42) | (81) | (92) |

[1]Field Ionization Mass Spectrometry

The level of liquid in the slurry reaction zone is maintained at desired levels by the continuous withdrawal of reactor-wax in slurry form from reactor 4 through line 6 where it is sent to catalyst/reactor wax separation zone 7 for recovery of catalyst which is recycled via line 3 to reactor 4. Separation of Fischer-Tropsch synthesis catalyst from the carrier liquid can be effected by filtration and/or magnetic separation. The heavy $C_{15+}$ liquid wax is sent to a wax cleanup section (not shown) which is adjacent to the zone 7 or physically removed therefrom. The wax cleanup typically involves a wax surge vessel equipped with agitator and heating system to maintain the wax at temperatures of 250° to 300° F. From the surge vessel, the wax is filtered to remove traces of the Fischer-Tropsch catalyst which otherwise may interfere in further processing of the wax.

The lighter products comprising all vaporous products (at the SFT conditions) are removed from reactor 4 through line 5 and may be passed into contact with a separate bed of a special zeolite catalyst identified and particularly represented by ZSM-5 zeolite where the hydrocarbons and oxygenates are selectively converted to high octane gasoline and distillate.

In accordance with the embodiment of FIG. 1, the reactor-wax recovered from the catalyst in zone 7 is introduced to reactor 10 via line 9 where it is catalytically converted by either hydrocracking or dewaxing the wax feed material. In both of these embodiments, the wax is introduced in liquid form to reactor 10 and is contacted with a hydrocracking or dewaxing catalyst under conversion conditions of temperature and pressure sufficient to produce fuel gas, gasoline and distillate products. The product effluent is removed via line 11 and is recovered and separated in a suitable product recovery fractionation operation 12 to obtain gasoline from line 13 and good quality distillate from line 14. Heavy hydrocarbons boiling above 650° F. are recycled from product recovery unit 12 via line 19 for admixture with feed wax 9 and light fuel gas is recovered as an overhead product through line 15.

In the hydrocracking embodiment, hydrogen is supplied to unit 10 from line 8. The catalysts used for hydrocracking are dual functional and comprise an acid component and a hydrogenation component. The hydrogenation component may be a noble metal such as platinum or palladium or a non-noble metal such as nickel, molybdenum or tungsten or a combination of these metals. The acidic cracking component may be an amorphous material such as an acidic clay or amorphous silica-alumina or, alternatively, a zeolite. Large pore faujasite zeolites such as zeolites X and Y have been conventionally used for this purpose because the principal components of the feedstock (wax) will enter the internal pore structure of the zoelites and undergo conversion. So, when waxy liquid feedstocks such as Fischer-Tropsch waxes are hydrocracked with a large pore catalyst such as Zeolite Y in combination with a hydrogenation component, the viscosity of the oil is reduced by cracking most of the 343° C.+ (about 650° F.) material into material that boils at 343° C. to 165° C. Typical hydrocracking catalysts are described in U.S. Pat. No. 4,486,296, U.S. Pat. No. 3,620,964 and U.S. Pat. No. 3,923,641, all of which are incorporated herein by reference.

Typical hydrocracking conditions include pressures of 500 to 3000 psig, temperatures of 600° to 900° F., weight hourly space velocities (WHSV) of 0.2 to 2.0 and hydrogen circulation rates of 500 to 20,000 SCF/B. Preferred conditions are pressures of 600 to 1500 psig, temperatures of 700° to 850° F., space velocities (WHSV) of 0.5 to 1.0 and hydrogen circulations of 1000 to 10,000 SCF/B.

In the dewaxing process, on the other hand, a small pore zeolite or a shape selective zeolite such as ZSM-5 is used as the acidic component of the catalyst and the normal and slightly branched chain paraffins which are present in the feedstock will be able to enter the internal pore structure of the zeolite so that they will undergo selective conversion in a single pass operation and thus minimize the yield of low value light gas. The paraffinic waxy components will therefore be converted and thus lower the pour point of the product. The catalyst preferably includes a hydrogenation component to induce hydrogenation reactions. The hydrogenation component may be a noble metal or a non-noble metal and is suitably of a conventional type, for example, nickel, tungsten, cobalt, molybdenum or combinations of these metals.

The dewaxing step used in the present invention is well known in the art and no further detailed description need be given other than to note the following patents, incorporated by reference, which describe the various catalysts and operating conditions which may be employed.

U.S. Pat. No. Re. 28,398 describes a process for catalytic dewaxing with a catalyst comprising a zeolite of the ZSM-5 type. A hydrogenation/dehydrogenation component may be present.

A process for hydrodewaxing a gas oil with a ZSM-5 type catalyst is described in U.S. Pat. No. 3,956,102.

A mordenite catalyst containing a Group VI or a Group VIII metal is used to dewax a low V.I. distillate from a waxy crude, as described in U.S. Pat. No. 4,110,056.

U.S. Pat. No. 3,755,138 describes a process for mild solvent dewaxing to remove high quality wax from a lube stock, which is then catalytically dewaxed to specification pour point.

Pending U.S. application Ser. No. 379,421, filed May 18, 1982, discloses a process for simultaneously hydrocracking and dewaxing hydrocarbon oils using a catalyst comprising zeolite beta composited with a metal hydrogenation component.

Typical dewaxing conditions include pressures of 50 to 3000 psig, temperatures of 450° to 900° F., weight hourly space velocities (WHSV) of 0.5 to 10.0 and hydrogen circulation rates of 100 to 5000 SCF/B. Preferred conditions are pressures of 300 to 1500 psig, temperatures of 500° to 800° F., space velocities (WHSV) of 1.0 to 5.0 and hydrogen pressures of 500 to 3000 SCF/B.

The conversion may be carried out by contacting the feedstock with a fixed stationary bed of catalyst, a fixed fluidized bed or with a transport bed. A simple configuration is a trickle-bed operation in which the feed wax is allowed to trickle through a stationary fixed bed. With such a configuration, it is desirable to initiate the reaction with fresh catalyst at a moderate temperature which is, of course, raised as the catalyst ages, in order to maintain catalytic activity. The catalyst may be regenerated by contact at elevated temperature with hydrogen gas, for example, or by burning in air or other oxygen-containing gas.

Figure 2:
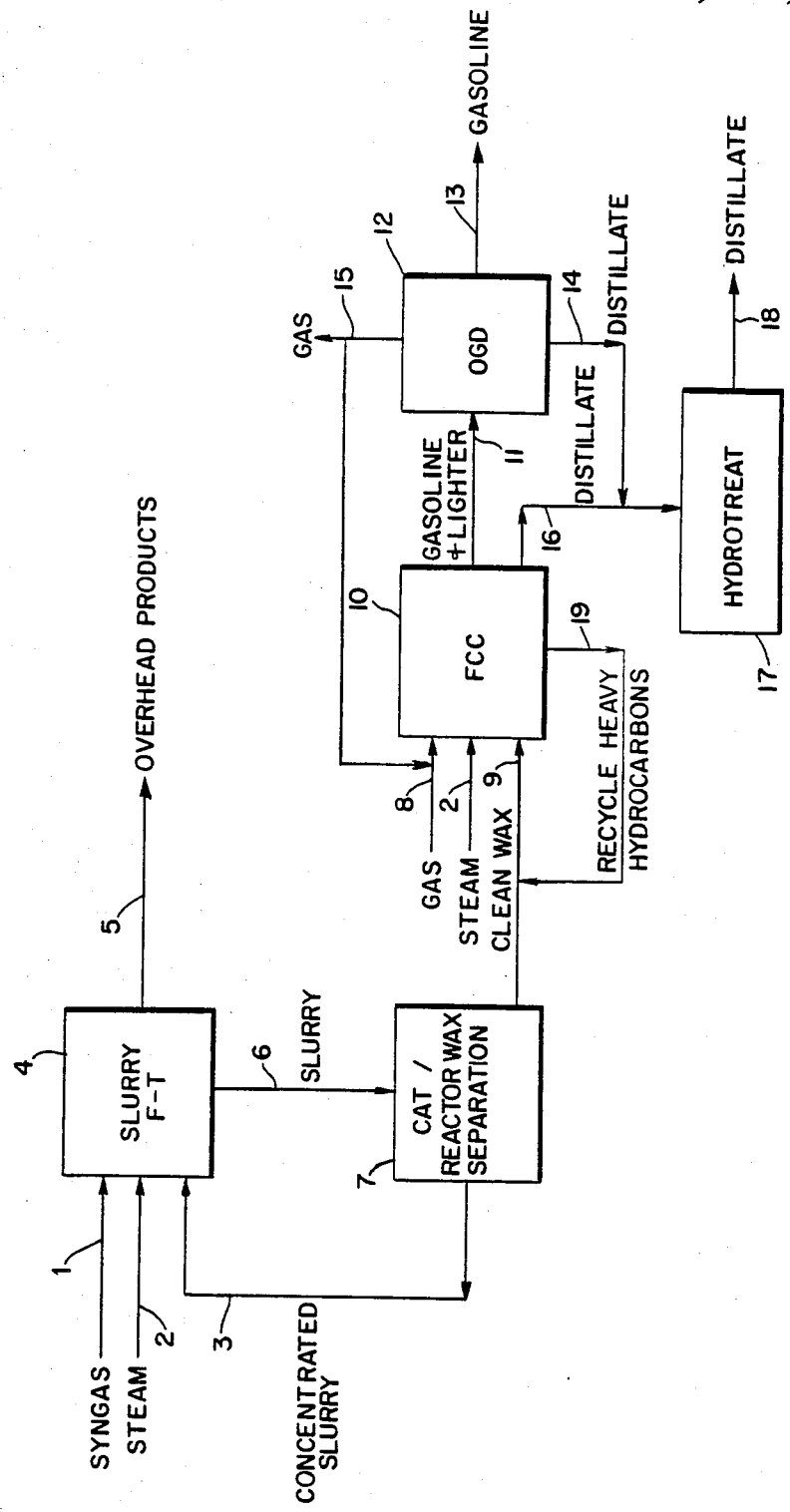
FIG. 2 is a flow diagram of another embodiment wherein the synthesis wax is upgraded by a combination process of fluid cracking with or without olefin polymerization.

In the embodiment shown in FIG. 2, the process scheme differs from FIG. 1 in the manner by which the wax is upgraded. As shown in FIG. 2, clean wax from line 9 is introduced together with steam and fuel gas through lines 2 and 8, respectively, to a fluidized cracking unit (FCC). The steam serves to disperse the liquid wax feed whereas the fuel gas is used to supply heat to FCC cracking unit 10. The overall liquid yields of hydrocarbon product from the cracking of Fischer-Tropsch wax is improved in unit 10 by minimizing the period of contact between the wax and the cracking catalyst. Fischer-Tropsch synthesis wax is so reactive that an optimum design of an FCC unit to crack the wax requires a very short reactor length, if cracking is done in a vertical riser, to give low reaction residence time. The catalyst used also requires a low activity; hence, conventional FCC catalyst discarded from a refinery FCC unit because of deactivation is eminently suitable. The coke deposited on the catalyst in cracking the Fischer-Tropsch wax is sufficiently low so that in regenerating it the heat resulting from burning the coke on the catalyst creates no problems of heat disposal. In fact, the addition of heat in the regeneration step is necessary, and it is estimated that a heat input of about 928 to 1,030 Btu/lb.-wax is needed to heat balance the FCC operation. Potential fuel sources include, among others, clean synthesis gas after the coal gasification and purification, and tail gases from product separation units. The amount of gas needed is small and for a gas containing 400 Btu heating value/SCF the amount will range from about 2.3 to 2.6 SCF/lb.-wax. For reasons of economy, synthesis gas is usually preferred over the more expensive downstream tail gases. The gasoline and fuel oil products obtained from the cracking process are of a higher quality in comparison to refinery cracking petroleum feedstocks. If the wax were cracked in a conventional refinery FCC unit under normal operating conditions, such as by blending with the refinery feedstock, overcracking occurs, leading to lower yields of liquid product. In brief, the liquid wax product obtained by separating the solid Fischer-Tropsch catalyst from admixture with the wax is cracked utilizing a low activity cracking catalyst under conditions calculated to yield a maximum of highly olefinic light gas and gasoline. The effluent from the cracking operation includes a heavy hydrocarbon fraction which is recycled to the wax feed mixture via line 19, a distillate fraction which is removed via line 16 for subsequent hydrotreating in unit 17 and an olefinic light gas and gasoline product which is withdrawn via line 11 and further processed in unit 12. The light gas and gasoline product is highly olefinic, predominating in $C_{2--}$ to $C_{11--}$ hydrocarbons, and contains substantial quantities of $C_{3--}$ to $C_{8--}$ olefins. If, however, olefins and gasoline are desired products, further processing in unit 12 would not be required.

The catalysts employed are well known materials and typically comprise a zeolite such as rare earth exchanged zeolite X or Y, ultra stable zeolite Y, the acid form of zeolite Y (HY), or other natural or synthetic faujasite zeolite. Preferably this is a rare earth exchanged zeolite X or Y.

Thus X or Y zeolites or other faujasite material used in the instant invention usually have the original cations associated therewith replaced by a wide variety of other cations according to techniques well known in the art. Typical replacing cations would include hydrogen, ammonium and metal cations including mixtures of the same. Of the replacing metallic cations, particular preference is given to cations of ammonium, hydrogen, rare earths, $Mg^{++}$, $Zn^{++}$, $Ca^{++}$, and mixtures thereof. Particularly preferred is rare earth exchanged zeolite Y.

Typical ion exchange techniques would be to contact the particular zeolite with a solution of a salt of the desired replacing cation or cations. Although a wide variety of salts can be employed, particular preference is given to the chlorides, nitrates and sulfates.

As noted above, a zeolite which may be used is the ultrastable zeolite Y. The ultrastable zeolites disclosed herein are well known to those skilled in the art. For example, they are described at pages 507-522, and pages 527-528 of the book *Zeolite Molecular Sieves* by Donald W. Breck, John Wiley & Sons, Inc. 1974 and are exemplified in U.S. Pat. Nos. 3,293,192 and 3,449,070. These two patents and the Breck reference above are incorporated herein by reference. These low sodium, ultra stable zeolites are available commercially from the W. R. Grace & Company.

The zeolites may be composited with a porous matrix material, such as alumina, silica-alumina, silica-magnesia, silica-zirconia, silica-thoria, silica-berylia, silica-titania, as well as ternary compositions, such as silica-alumina-thoria, silica-alumina-zirconia, magnesia and silica-magnesia-zirconia. The matrix may be in the form of a cogel. The relative proportions of zeolite component and inorganic oxide gel matrix on an anhydrous basis may vary widely with the zeolite content ranging from 10 to 99, more usually 25 to 80, percent by weight of the dry composite. The matrix itself may possess catalytic properties, generally of an acidic nature.

The cracking operation is carried out using preferably a low activity cracking catalyst. An activity (FAI) of between 20 and 60 can be used, the preferred 25 to 50. The fluid activity index (FAI) is a method used to measure the relative cracking activity of fluidized catalyst.

As used herein, the fluid activity index (FAI) is defined as the percent (by volume) conversion of Light East Texas gas oil obtained by cracking under the following conditions:

| | |
|---|---|
| Temperature | 454° C. |
| Catalyst to oil wt. ratio | 2.0 |

-continued

| | |
|---|---|
| Weight hourly space velocity | 6.0 hr$^{-1}$ |
| Process period | 5.0 min. |
| Pressure | 1.0 atm. |

The test is run in a fixed fluidized bed reactor containing 180 grams of the test catalyst. The conversion is based on distilling gasoline with a 400° F. ASTM (EP) end point.

A typical equilibrium cracking catalyst has an FAI of about 65-75. Equilibrium catalysts removed from a fluid cracking unit for disposal have an FAI of 40-55 burned clean. The FAI of the catalyst is inadequate for the exacting requirements of a cracking unit, but clearly much of the activity remains. This catalyst which otherwise would be disposed of is an example of the catalysts which can be used in the present invention.

Typical cracking conditions include pressures of 10 to 60 psig, temperatures of 800° to 950° F., cat/oil ratios of 3 to 8 and catalyst residence times of 0.5 to 5 seconds. Preferred conditions are pressured of 20 to 50 psig, temperatures of 800° to 900° F., cat/oil ratios of 4 to 8 and catalyst residence times of 0.5 to 4 seconds.

Following the cracking step, the olefinic light gas and gasoline distillate produced in reactor 10 is removed via line 11 and introduced into catalytic reactor 12 where it is contacted with a ZSM-5 type catalyst at a temperature, pressure and WHSV (weight hourly space velocity) within the following ranges:

| Ranges | Broad | Preferred |
|---|---|---|
| Temperature, °F. | 300° to 700° | 375° to 600° |
| Pressure, psig | 200 to 2000 | 600 to 1000 |
| WHSV (based on olefins) | 0.3 to 5 | 0.5 to 2.5 |

The olefinic light gas and gasoline undergo conversion wherein at least 10 wt.% of the charge material is converted to material boiling above about 350° F., which conversion occurs when the set of operating conditions used is severe enough to induce a decrease of the specific volume of the remaining treated $C_5$ to 300° F. cut by at least 0.05 cc/g, and preferably by at least 0.07 cc/g, when compared with the same cut of untreated material measured at 70° F. Such conditions not only produce a substantial fuel oil fraction but also result in a gasoline that has substantially less than half of the original content of olefins.

The catalytic conversion of an olefinic charge material to gasoline and distillate (OGD) is known in the art and the following patents which describe this conversion are incorporated by reference.

U.S. Pat. No. 4,254,295, to Tabak, describes the use of ZSM-12 in the liquid phase oligomerization of straight and branched chain olefins which may have from 20 to 12 carbon atoms, but preferably from 2 to 6 carbon atoms; U.S. Pat. No. 4,227,992 to Garwood et al describes the separation of ethylene in admixture with light olefins by contacting the mixture with a member of the special class of zeolites used in the present invention. U.S. Pat. No. 4,211,640 to Garwood discloses that the gum stability property of a highly olefinic gasoline is improved by contact with the forementioned type catalyst under reaction conditions carefully selected so as to substantially avoid formation of either aromatic hydrocarbons or products lighter than $C_6$. Some fuel oil is formed in this process.

A distillate fraction removed from reactor 10 via line 16 is combined with a distillation fraction 14 from reactor 12 and the combined mixture is hydrotreated in reactor 17 to provide an improved distillate which is recovered via line 18. High quality gasoline is recovered from line 13 and light fuel gas from line 15 may, if desired, be recycled to line 8 to provide the necessary heat balance for the FCC operation.

The hydrotreating step may be conducted at a pressure within the range of 50 to 3000 psig and preferably between 300 and 1500 psig. The temperature is generally within the range of 100° to 800° F., with the temperature preferably being within the range of 200° to 600° F. The feed is generally conducted through the catalyst reactor at an overall space velocity (WHSV) between 0.5 and 10 and preferably between 1.0 and 5, with hydrogen being present in an amount between 100 and 5000 standard cubic feet per barrel of feed, preferably 500 to 3000 SCF/B.

The catalysts employed are conventional hydrotreating catalysts which comprise one or more metals, metal oxides or metal sulfides from the metals of Group VIB and Group VIII on a solid support such as alumina, silica, titania, zirconia or mixtures thereof. Representative Group VIB metals include molybdenum, chromium and tungsten and Group VIII metals include nickel and cobalt. These metal components are in the form of metals or metal oxides, or metal sulfides on the indicated supports in amounts generally between 1 and 30 percent by weight.

Hydrotreating of the distillate feed serves to convert heteroatom hydrocarbon derivatives to gaseous products and converts some hydrocarbons to lighter fractions.

The following examples illustrate the best mode now contemplated for carrying out the invention.

EXAMPLE 1

The wax product from Run 4 of Table 3 was converted over ZSM-5 at dewaxing conditions to obtain large yields of moderate octane gasoline and good quality distillate. The gasoline and distillate products and distillate qualities are shown below in Tables 4 and 5.

TABLE 4

Hydrodewaxing of Fischer-Tropsch Reactor Wax[1]

| | Run No. | | |
|---|---|---|---|
| | 1 | 2 | 3 |
| Days on Stream | 1.7 | 2.6 | 3.5 |
| Temperature, °C. | 343 | 330 | 316 |
| Recovery, Wt. % | 93.5 | 103.4 | 104.8 |
| Conversion, Wt. %[2] | 70.8 | 31.6 | 14.9 |
| $H_2$ Consumption, NL/L Conv. | 51 | — | — |
| Selectivity, Wt. % (G + D + $C_4$—) | | | |
| $C_1$ | 0 | 0 | 0 |
| $C_2/C_2=$ | 1.0/0 | 0.6/0 | 0.4/0 |
| $C_3$-$C_4$ Olef. | 1.0 | 3.3 | 4.4 |
| $C_3$ | 6.7 | 6.1 | 7.4 |
| $iC_4$ | 10.6 | 7.2 | 6.5 |
| $nC_4$ | 10.8 | 7.3 | 2.5 |
| $C_5$-177° C. | 58.6 | 61.2 | 52.9 |
| 177-344° C. | 11.3 | 14.3 | 25.9 |
| Total | 100.0 | 100.0 | 100.0 |

[1] 5 cc Microreactor, Ni/ZSM-5 Catalyst, 2.86 MPa, 1.0 LHSV, (1/hr) 422 NL $H_2$/L, Run CT-256-4 Wax
[2] Based on 344° C.$^-$ Product

TABLE 5

Products From Hydrodewaxing of Fischer-Tropsch Reactor-Wax

| | Run No. | | |
|---|---|---|---|
| | 1 | 2 | 3 |
| T. °C. | 343 | 330 | 316 |
| Distillate | | | |
| Cetane Index | 33 | 61 | 68 |
| Pour Point, °C. | −130 | −30 | 6 |
| Raw Gasoline | | | |
| Paraffin, Wt. % | 61.1 | 55.9 | 51.8 |
| Olefin | 7.9 | 27.0 | 39.6 |
| Naphthene | 5.5 | 2.8 | 2.0 |
| Aromatic | 25.5 | 14.3 | 6.6 |
| Octane No. (R + O) | 80.7 | 82.3 | 85.9 |

EXAMPLE 2

The wax product in Run 4 of Table 3 was also hydrocracked over a zeolite catalyst into gasoline and distillate products as shown below in Table 6. The gasoline and distillate qualities are further shown in Table 7.

TABLE 6

Hydrocracking of Fischer-Tropsch Reactor-Wax[1]

| | Run No. | | | | |
|---|---|---|---|---|---|
| | 1 | 2 | 3 | 4 | 5 |
| Days on Stream | 1.7 | 2.7 | 3.4 | 5.0 | 5.7 |
| Temperature, °C. | 371 | 344 | 329 | 330 | 329 |
| LHSV, 1/hr. | .5 | .5 | .5 | 1 | 2 |
| Recovery, Wt. % | 95.3 | 105.2 | 93.8 | 98.4 | 97.7 |
| Conversion, Wt. %[2] | 98.9 | 98.0 | 80.0 | 12.1 | 5.8 |
| $H_2$ Consumption, NL/L Conv. | 234 | 200 | 151 | — | 34 |
| Selectivity, Wt. % | | | | | |
| (G + D + $C_4$—) | | | | | |
| $C_1$ | 0.5 | 0.1 | 0.1 | 0 | 0 |
| $C_2/C_2=$ | 1.2/0 | 0.3/0 | 0.3/0 | 0/.4 | 0/0 |
| $C_3$-$C_4$ Olefins | 0.7 | 0.6 | 0.4 | .8 | 0 |
| $C_3$ | 7.5 | 3.3 | 4.0 | 7.3 | 4.9 |
| $iC_4$ | 18.1 | 16.0 | 15.0 | 11.9 | 8.9 |
| $nC_4$ | 24.2 | 10.9 | 5.0 | 1.4 | 0 |
| $C_5$-177° C. | 46.8 | 66.4 | 65.2 | 53.8 | 37.1 |
| 177–344° C. | 1.0 | 2.4 | 10.0 | 24.4 | 49.1 |
| Total | 100.0 | 100.0 | 100.0 | 100.0 | 100.0 |

[1]10 cc Microreactor, Group VI-A and VIII-A metal impregnated faujasite/SiAl, 4.58 MPa, 0.5 LHSV, 675 NL $H_2$/L
[2]Based on 344° C.⁻ Product

TABLE 7

Products From Hydrocracking of Fischer-Tropsch Reactor-Wax

| | Run No. | | | | |
|---|---|---|---|---|---|
| | 1 | 2 | 3 | 4 | 5 |
| LHSV, 1/hr. | 0.5 | 0.5 | 0.5 | 1 | 2 |
| T, °C. | 371 | 344 | 329 | 330 | 329 |
| Distillate | | | | | |
| Cetane Index | 34 | — | 65 | 51 | 59 |
| Pour Point, °C. | −52 | −32 | −36 | −11 | −2 |
| Raw Gasoline | | | | | |
| Paraffin, Wt. % | 96.5 | 91.5 | 89.7 | — | — |
| Olefin | .05 | 3.6 | 6.1 | — | — |
| Naphthene | .05 | 3.1 | 4.1 | — | — |
| Aromatic | 2.4 | 1.8 | .1 | — | — |
| Octane No. (R + O) | 83.9 | 80.8 | 73.5 | — | — |

EXAMPLE 3

The synthesis wax product from Run 4 in Table 3 was further hydrocracked over a cobalt and molybdenum impregnated alumina catalyst as shown in Table 8. This catalyst provided a large yield of high quality distillate and a low octane naphtha which may be advantageously combined with the Fischer-Tropsch overhead product in line 5 for further processing and selective conversion to high gasoline and distillate fuel. The gasoline and distillate qualities are shown in Table 9.

TABLE 8

Hydrocracking of Fischer-Tropsch Reactor-Wax[1]

| Days on Stream | 0.8 | 1.7 | 2.6 | 3.5 | 4.4 | 5.3 |
|---|---|---|---|---|---|---|
| Temperature, °C. | 342 | 371 | 400 | 414 | 426 | 454 |
| Recovery, Wt. % | 98.9 | 101.3 | 99.3 | 99.6 | 99.0 | 98.5 |
| Conversion, Wt. %[2] | 3.2 | 4.1 | 6.4 | 110 | 18.9 | 71.5 |
| Selectivity, Wt. % | | | | | | |
| (G + D + $C_4$—) | | | | | | |
| $C_1$ | 3.2 | 4.7 | 4.5 | 3.7 | 2.6 | 1.9 |
| $C_2/C_2=$ | 4.4/0 | 1.6/4.9 | 3.5/0 | 3.5/0 | 1.0/0 | 2.2/0 |
| $C_3$-$C_4$ | 0 | 0.8 | 0.7 | 0.9 | 0 | 0.3 |
| $C_3$ | 0 | 1.9 | 2.0 | 2.4 | 3.0 | 2.3 |
| $iC_4$ | 1.6 | 0 | 2.5 | 3.1 | 1.9 | 0.2 |
| $nC_4$ | 0 | 0 | 0 | 0 | 0 | 0.6 |
| $C_5$-177° C. | 8.2 | 2.7 | 5.0 | 3.9 | 7.5 | 16.2 |
| 177–344° C. | 82.6 | 83.4 | 81.8 | 82.6 | 84.0 | 76.3 |
| Total | 100.0 | 100.0 | 100.0 | 100.0 | 100.0 | 100.0 |

[1]10 cm³ Microreactor, Ketjen 742 Catalysts, 4.58 MPa, 0.5 LHSV, 675 NL $H_2$/L
[2]Based on 344° C.⁻

TABLE 9

Products from Hydrocracking of Fischer-Tropsch Reactor-Wax

| Days on Stream | .8 | 1.7 | 2.6 | 3.5 | 4.4 | 5.3 |
|---|---|---|---|---|---|---|
| Temperature, °C. | 342 | 371 | 400 | 413 | 426 | 454 |
| Conversion, Wt. %[1] | 3.2 | 4.1 | 6.4 | 11.0 | 18.9 | 71.5 |
| $H_2$ Consumption, NL/L | — | — | — | — | — | 110 |
| Selectivity, Wt. % . | | | | | | |
| G + D + $C_4$— | | | | | | |
| $C_4$— | 9.2 | 13.9 | 13.2 | 13.5 | 8.5 | 7.5 |
| $C_5$-177° C. Gasoline | 8.2 | 2.7 | 5.0 | 3.9 | 7.5 | 16.2 |
| 177–343° C. Distillate | 82.6 | 83.4 | 81.8 | 82.6 | 84.0 | 76.3 |
| Total | 100.0 | 100.0 | 100.0 | 100.0 | 100.0 | 100.0 |
| Product Properties | | | | | | |
| $C_5$-177° C. Gasoline | | | | | | |
| P | — | — | — | — | 63.3 | 69.3 |
| O | — | — | — | — | 14.9 | 3.2 |
| N | — | — | — | — | 9.7 | 13.1 |
| A | — | — | — | — | 12.1 | 14.4 |
| R + O | — | — | — | — | 39 | 35 |
| 177–343 C Distillate | | | | | | |
| Cetane Index | — | — | — | — | 68 | 72 |
| Pour Point, °C. | 4 | 3 | −14 | −1 | −6 | −16 |

[1]Based on 343° C.⁻ Product

EXAMPLE 4

The wax product in Run 4 was catalytically cracked in an FCC unit having a short riser in which synthesis gas, or other fuel, was burned in the FCC regenerator to create the needed heat for heat balancing the FCC operation. The catalyst was of moderate activity and was a composite of silica-alumina and rare earth faujasite. Under the operating conditions of temperature, pressure, etc., shown in Table 10, the short FCC riser converted the highly paraffinic synthesis wax from line 9 into a highly olefinic light gas and gasoline and a distillate product.

TABLE 10

FCC Conversion of Fischer-Tropsch Wax

| CAT | HEZ-53 |
|---|---|
| T, °C. | 465–478 |
| P, MPa | 0.11 |
| Cat/Oil | 4.2 |
| Res. Time, s | 1 |
| Conversion, % | 91 |
| Selectivity, wt. % | |
| $C_2$— | 2.0 |
| $C_3$-$C_4$ Olef. | 13.1 |
| $C_3°$ + $nC_4°$ | 1.7 |
| $iC_4°$ | 2.5 |
| $C_5$+-194° C. | 57.2 |

TABLE 10-continued

| FCC Conversion of Fischer-Tropsch Wax | |
| --- | --- |
| 194–344° C. | 23.5 |
| Total | 100.0 |
| $C_5+$ -194° C. | |
| PONA | 25/63/4/8 |
| Octane, R + O | 90 |
| 194–344° C. | |
| Pour, °C. | −25 |
| Cetane Index | 50 |

EXAMPLE 5

The olefinic light gas and gasoline withdrawn from FCC unit 10 via line 11 in Example 4 is converted into high quality gasoline and distillate products under the operating conditions shown in Table 11. The product selectivities in the conversion of olefins to gasoline and distillate (OGD) are estimated based on comparative data for the conversion of $C_2$-$C_9$ olefins.

TABLE 11

| FCC/OGD Conversion of Fischer-Tropsch Wax | |
| --- | --- |
| OGD | |
| CAT | ZSM-5 |
| T, °C. | 205 |
| P, MPa | 5.62 |
| WHSV | 1 |
| $H_2$, NL/L | 40 |
| Selectivities, wt. % | |
| $C_2-$ | 1.8 |
| $C_3$-$C_4$ Olef | 2.0 |
| $C_3^\circ$ + $nC_4^\circ$ | 2.1 |
| $iC_4^\circ$ | 2.6 |
| $C_5+$ -194° C. | 39.2 |
| 194–344° C. | 52.3 |
| Total | 100.0 |
| $C_5+$ -194° C. | |
| PONA | 36/45/6/13 |
| Octane, R + O | 92 |
| 194–344° C. | |
| Pour, °C. | −25 |
| Cetane Index | 50 |

What is claimed is:

1. A process for converting synthesis gas to liquid hydrocarbons comprising the steps of:
   (a) charging said synthesis gas to a Fischer-Tropsch synthesis conversion zone containing a catalyst providing CO reducing characteristiccs to produce a waxy hydrocarbon liquid;
   (b) separating hydrocarbon wax from said waxy liquid;
   (c) catalytically cracking said wax in a fluidized bed of acid crystalline zeolite at cracking temperature under process conditions requiring a supply of heat to effect cracking, thereby producing olefinic liquid hydrocarbon crackate in the gasoline and distillate boiling range along with olefinic light gas;
   (d) recovering distillate range hydrocarbons from the liquid crackate;
   (e) further converting the olefinic gasoline range hydrocarbon crackate and olefinic light gas under oligomerization conditions in contact with a shape selective medium pore acid oligomerization catalyst to upgrade at least a portion of said olefinic crackate and olefinic light gas to distillate range hydrocarbon product and producing by-product light fuel gas;
   (f) separating said light fuel gas from step (e) and passing said light fuel gas to cracking step (c) to supply heat thereto.

2. The method of claim 1 which comprises contacting said wax in step (e) with a faujasite cracking catalyst having a fluid activity index of between about 20 and about 60, a temperature between about 800° and 950° F., a pressure of about 10 to 60 psig, and a catalyst residence time of about 0.5 to about 5 seconds to produce an olefinic light gas and gasoline distillate.

3. The method of claim 1 which comprises contacting said olefinic light gas and olefinic gasoline in step (e) with a crystalline zeolite catalyst having a Constraint Index of 1 to 12 and a silica to alumina ratio of at least about 12 under a combination of reaction conditions that include a temperature of about 300° F. to about 700° F., a pressure of 200 to 2000 psig, and a WHSV of about 0.3 to 5, said combination of conditions being effective to decrease the specific volume of the $C_5+$ to 300° F. cut of liquid hydrocarbon by at least 0.05 cc/g; and thereafter recovering a high quality gasoline and distillate product.

4. The method of claim 3 wherein said oligomerization conversion is carried out with a crystalline aluminosilicate zeolite selected from the group consisting of ZSM-5, ZSM-11, ZSM-12, ZSM-21, ZSM-23, ZSM-35, ZSM-38 and ZSM-48.

5. The method of claim 1 wherein the synthesis gas reaction of step (a) is carried out with a low $H_2$/CO ratio syngas in a slurried liquid phase catalyst reaction system.

* * * * *